(12) United States Patent
Gayet et al.

(10) Patent No.: US 8,071,817 B2
(45) Date of Patent: Dec. 6, 2011

(54) PREPARATION OF PURIFIED HYDROQUINONE AND FORMING OF SAME

(75) Inventors: Hubert Gayet, Villeurbanne (FR); Bruno Heinisch, Villeurbanne (FR); Jean-Claude Le Thiesse, Saint-Etienne (FR)

(73) Assignee: Rhodia Operations, Aubervilliers Cedex (FR)

( * ) Notice: Subject to any disclaimer, the term of this patent is extended or adjusted under 35 U.S.C. 154(b) by 10 days.

(21) Appl. No.: 12/306,770

(22) PCT Filed: Jun. 27, 2007

(86) PCT No.: PCT/FR2007/001079
§ 371 (c)(1),
(2), (4) Date: Jun. 30, 2009

(87) PCT Pub. No.: WO2008/000955
PCT Pub. Date: Jan. 3, 2008

(65) Prior Publication Data
US 2009/0306436 A1    Dec. 10, 2009

(30) Foreign Application Priority Data
Jun. 29, 2006   (FR) ..................................... 06 05865

(51) Int. Cl.
*C07C 37/74* (2006.01)
(52) U.S. Cl. ........ 568/753; 568/750; 568/751; 568/752; 568/763

(58) Field of Classification Search ........................ None
See application file for complete search history.

(56) References Cited

U.S. PATENT DOCUMENTS

| | | | |
|---|---|---|---|
| 4,308,110 A * | 12/1981 | Hosaka et al. | .................. 203/48 |
| 5,698,142 A | 12/1997 | Prager et al. | |
| 6,844,472 B1 | 1/2005 | Bourdon et al. | |
| 7,235,299 B2 | 6/2007 | Le Thiesse | |

FOREIGN PATENT DOCUMENTS

| | | |
|---|---|---|
| EP | 0 740 954 A1 | 11/1996 |
| FR | 2 788 763 A1 | 7/2000 |
| FR | 2 846 324 A1 | 4/2004 |
| GB | 2 083 816 A | 3/1982 |
| JP | 2000302716 | 10/2000 |

OTHER PUBLICATIONS

International Search Report dated Nov. 15, 2007 issued in PCT/FR2007/001079.

* cited by examiner

*Primary Examiner* — Brian J Davis
(74) *Attorney, Agent, or Firm* — Buchanan Ingersoll & Rooney, P.C.

(57) ABSTRACT

Purified hydroquinone is prepared and formed from raw compounds essentially containing hydroquinone associated with very small quantities of impurities including resorcinol and pyrogallol, and includes a distillation purification step in which the resorcinol and pyrogallol are eliminated, directly followed by a step in which the purified hydroquinone is formed.

32 Claims, 6 Drawing Sheets

PRIOR ART

PREPARATION OF PURIFIED HYDROQUINONE AND FORMING OF SAME

CROSS-REFERENCE TO PRIORITY/PCT APPLICATIONS

This application claims priority under 35 U.S.C. §119 of FR 0605865, filed Jun. 29, 2006, and is a continuation/national phase of PCT/FR 2007/001079, filed Jun. 27, 2007 and designating the United States (published in the French language on Jan. 3, 2008, as WO 2008/000955 A1; the title and abstract were also published in English), each hereby expressly incorporated by reference in its entirety and each assigned to the assignee hereof.

A subject matter of the present invention is a process for preparing purified hydroquinone and forming.

The invention is targeted at providing hydroquinone freed from the impurities resulting from its process of preparation and forming.

According to one embodiment, the invention provides a process which makes it possible to obtain hydroquinone of high purity and forming.

Hydroquinone (or 1,4-dihydroxybenzene) is a product widely used in numerous fields of application as polymerization inhibitor or antioxidant in elastomers or as synthetic intermediate. Another field of application is photography. It follows that this is a staple product.

Different purities are required according to the market concerned.

This is because, while a technical hydroquinone, that is to say including a few impurities, in order to minimize operating costs, is satisfactory for some applications, other applications, in particular photography, require a very high degree of purity.

Thus, the hydroquinone must, in some cases, meet requirements of high purity which can be fairly restrictive.

The problem which is posed is that purification is not easy to carry out as hydroquinone is an oxidation-sensitive product and quickly results in decomposition products which are colored.

In the crude hydroquinone to be purified according to the invention, essentially hydroquinone is present, that is to say at least 90% by weight of hydroquinone is present, the remainder being composed of the impurities to be removed. Preferably, the crude hydroquinone comprises at least 96% by weight of hydroquinone.

In point of fact, there is great difficulty in removing extremely low contents of impurities.

Furthermore, the difficulty is increased due to the nature of the impurities. The compounds to be separated have similar volatilities as hydroquinone isomers are present and pyrogallol is also present among the impurities to be removed.

In point of fact, the separation of the pyrogallol present in the mixture of the impurities to be removed presents a problem to a person skilled in the art. This is because pyrogallol is a compound which thermally decomposes even more readily than hydroquinone and its decomposition results in colored impurities.

Furthermore, different physicochemical characteristics in terms of particle size, flowability or rate of dissolution may be required depending on the applications.

Hydroquinone is currently available commercially in the form of a powder formed of small and brittle needles. The disadvantages which result therefrom are the presence of fines, which result in problems of dust formation during storage and handling of said powder.

In point of fact, hydroquinone dust is not without danger with respect to the environment, due to risk of explosion, and with respect to man, as this substance is irritating to the eyes and respiratory tract and may also cause irritation of the skin when it is brought into contact with the latter.

Thus, the market requires hydroquinone exhibiting a high purity but riot exhibiting the problems related to the handling of a powder.

One of the synthetic routes to hydroquinone consists in hydroxylating phenol with hydrogen peroxide, in particular in the presence of homogeneous or heterogeneous acid catalysts.

Thus, recourse may be had, as according to FR 2 071 464, to a strong protic acid, that is to say an acid exhibiting a pKa in water of less than 0.1, preferably of less than −1.

Mention may be made, as example of strong protic acids, inter alia, of sulfuric acid, chlorosulfuric acid, perchloric acid or sulfonic acids, such as, for example, methanesulfonic, trifluoroinethanesulfonic, toluenesulfonic or phenolsulfonic acid.

Mention may be made, as other examples of protic acid catalysts, of sulfonic resins and more particularly the resins sold under various trade names. Mention may be made, inter alia, of the following resins: Temex 50, Amberlyst 15, Amberlyst 35, Amberlyst 36 and Dowex 50W.

The abovementioned resins are composed of a polystyrene backbone which carries functional groups which are sulfonic groups. The polystyrene backbone is obtained by polymerization of styrene and divinylbenzene, under the influence of an activation catalyst, generally an organic peroxide, which results in a crosslinked polystyrene which is subsequently treated with concentrated sulfuric acid or hydrochloric/sulfuric acid, resulting in a sulfonated styrene/divinylbenzene copolymer.

It is also possible to resort to sulfonic resins which are phenol/formaldehyde copolymers and which carry a methylenesulfonic group on the aromatic ring, for example the resin sold under the name Duolite Arc 9359.

Other commercially available resins are also suitable and mention may be made of perfluorinated resins carrying sulfonic groups and more particularly Nafion which is a copolymer of tetrafluoroethylene and of perfluoro[2-(fluorosulfonylethoxy)propyl]vinyl ether.

Mention may be made, as other catalysts suitable in hydroxylation processes, of iron(II) and copper(II) complexes (FR 2 121 000, USSR 1 502 559) and any other catalyst of Fenton type.

Other processes for the preparation of hydroquinone involve heterogeneous catalysis. Thus, use may be made of an acid zeolite of titanium silicalite (or titanosilicalite-1) type or of iron silicalite type of TS-1 type (FR 2 489 816), a zeolite of titanium silicalite MEL type (EP 1 131 264) or a titanozeosilite of MFI type (EP 1 123 159). It is also possible to use an MCM-22 zeolite (FR 2 856 681).

On conclusion of such hydroxylation reactions, a mixture is obtained which essentially comprises pyrocatechol (or 1,2-dihydroxybenzene) and hydroquinone, in variable proportions with in general a pyrocatechol/hydroquinone ratio by weight of the order of 0.25 to 4.0, and also various by-products in much smaller amounts, in particular resorcinol (or 1,3-dihydroxybenzene) and pyrogallol (or 1,2,3-trihydroxybenzene), generally at contents of 0.5 to 4.0% by weight, percentages expressed with respect to the amount of hydroquinone and pyrocatechol formed.

Mixtures of variable compositions are obtained which comprise, by weight, from 20 to 80% of pyrocatechol, from 80 to 20% of hydroquinone, from 0.1 to 2% of resorcinol and from 0.1 to 2% of pyrogallol.

Typically, mixtures are obtained which comprise, by weight, from 50 to 80% of pyrocatechol, from 20 to 50% of hydroquinone, from 0.1 to 2% of resorcinol and from 0.1 to 2% of pyrogallol.

In order to isolate the hydroquinone from crude mixtures of this type, one method currently known consists in distilling said mixture, making it possible to obtain, as distillation top product, pyrocatechol (which is the most volatile compound in the mixture) and, as distillation bottom product, a "crude hydroquinone", namely a mixture essentially comprising hydroquinone, in combination with small amounts of impurities (in particular resorcinol and pyrogallol, and also possible traces of pyrocatechol not removed by the distillation).

The invention provides, starting from this crude hydroquinone, for the provision of hydroquinone which can have a very high purity and which is presented in a form which makes it possible to avoid the problems related to the handling of a powder.

There has now been found, and it is this which constitutes the subject matter of the present invention, a process for the preparation of purified hydroquinone put into the form of flakes, starting from a crude hydroquinone essentially comprising hydroquinone and small amounts of impurities, including at least resorcinol, pyrogallol and traces of pyrocatechol, characterized in that it comprises the following stages:

a stage of purification of the crude hydroquinone by distillation, comprising:
(A) a topping distillation, in which the crude hydroquinone $HQ^0$ is injected into a distillation column and where the resorcinol is removed as distillation top product, optionally in conjunction with all or part of the other light impurities, whereby a crude mixture M, comprising hydroquinone and the heavy impurities, is recovered at the column bottom; and
(B) a tailing distillation, in which the crude mixture M obtained in stage (A) is injected into a distillation column and where the pyrogallol is removed at the column bottom, optionally in conjunction with all or part of the other heavy impurities, whereby hydroquinone in a purified form (HQ) is recovered at the column top;

a stage of forming the purified hydroquinone obtained at the distillation outlet, by deposition of the latter as a film on a support made of a thermally conductive material or coated with a thermally conductive material, followed by the solidification thereof by bringing the support to the appropriate temperature, then recovery of the solidified hydroquinone in the form of flakes, using any appropriate means.

Thus, the invention provides a process which links together a stage of purification by distillation, followed immediately by the forming thereof.

The result of this is that the hydroquinone is not subjected to an additional melting operation generally required for the forming. The process of the invention, which employs hydroquinone resulting directly from the distillation, avoids possible decomposition and possible subsequent colorations.

Figure 1:
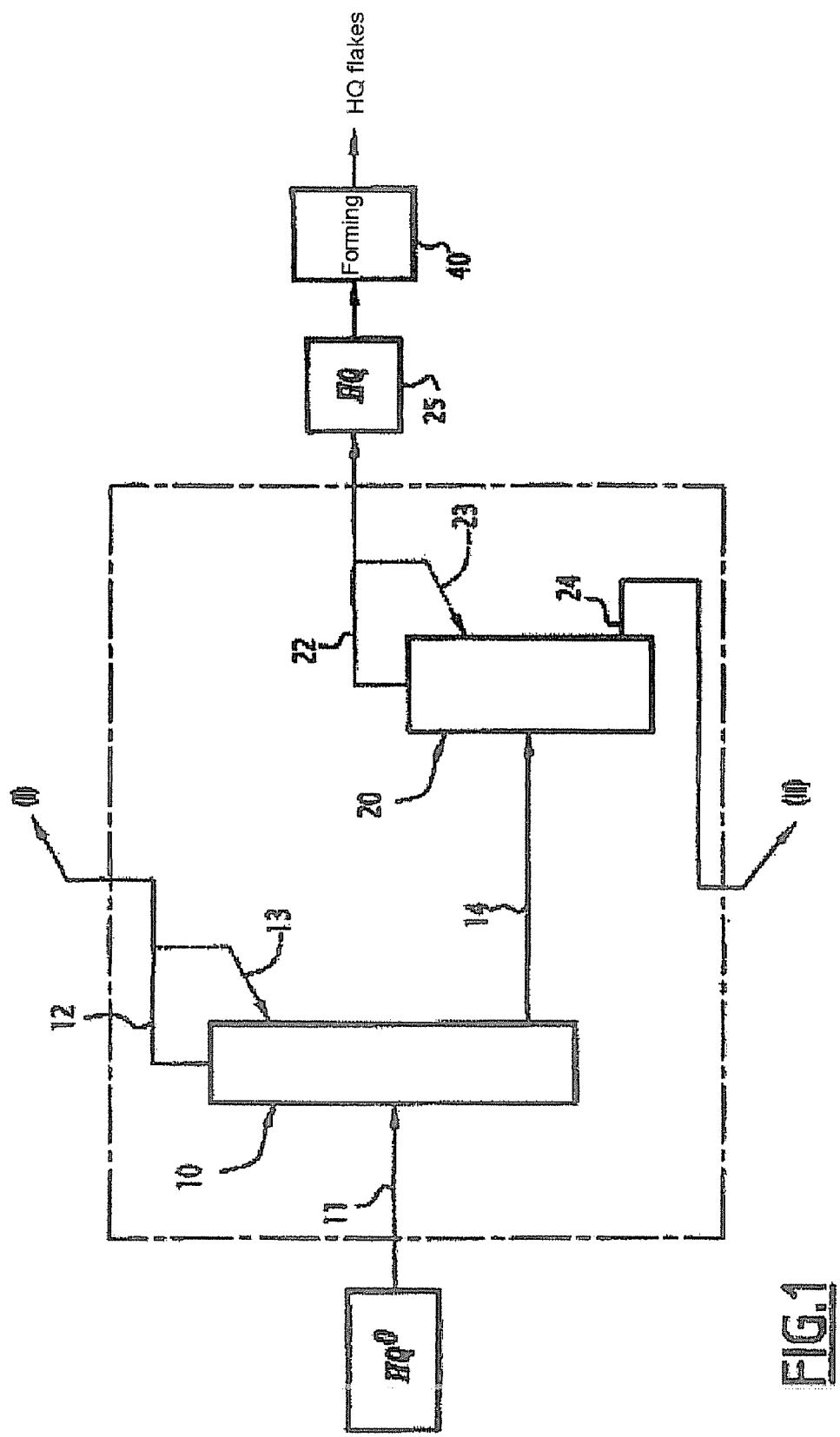
FIG. 1 is a diagrammatic representation of the general device used according to the invention for the implementation of the distillation stages (A) and (B) and of the stage for forming the hydroquinone resulting from the distillation.

The process provided by the invention is simple and less expensive in capital costs in comparison with other forming techniques, such as the prilling described in EP-A 1 556 322.

The hydroquinone obtained exhibits a high purity and can be easily handled.

In accordance with the process of the invention, in a first stage of the process of the invention, the crude hydroquinone is purified.

According to the first stage of the process of the invention, it is possible to purify a crude hydroquinone ($HQ^0$) essentially comprising hydroquinone in a proportion of at least 90% by weight and small amounts of impurities of less than 10% by weight, where the impurities present simultaneously include:
(i) impurities having a lower evaporation temperature than that of hydroquinone, referred to hereinafter as "light impurities", including in particular resorcinol, preferably as major impurity among the light impurities; and
(ii) impurities having a higher evaporation temperature than that of hydroquinone, hereinafter denoted by "heavy impurities", including in particular pyrogallol, preferably as major impurity among the heavy impurities.

In accordance with the invention, the purification stage of the process of the invention comprises a topping distillation (A) and a tailing distillation (B).

The inventors have found that the use of the successive distillation stages (A) and (B) above makes it possible to obtain efficient purification of hydroquinone, with the possibility of removing extremely low amounts of impurities comprising a mixture of compounds more volatile than hydroquinone and of compounds less volatile than hydroquinone, of resorcinol and pyrogallol type.

In this context, it should be noted that the process of the invention can be used to treat crude hydroquinones comprising of the order of 0.5 to 4% by weight of impurities, for example amounts of impurities as low as from 0.5 to 2% by weight, in order to result, in fine, in purified hydroquinones generally comprising less than 4000 ppm of impurities, most often less than 3000 ppm.

More specifically, the purification according to the invention can in particular be employed in the preparation of hydroquinones of high purity comprising impurities at a content of less than 2500 ppm, typically at most of the order of 2000 ppm, preferably at most of the order of 1500 ppm and more preferably at most of the order of 1000 ppm, indeed even less.

The possibility of such an efficiency in separation proves to be relatively unexpected, insofar as the problem which was posed in terms of separation was particularly difficult to solve, in particular in view of the fact that the various compounds to be separated have very similar relative volatilities.

In addition, hydroquinone exhibits a high melting point (172.5° C.) and a very high evaporation point, even under reduced pressure (258° C. under 500 millibar; 208° C. under 100 millibar).

More unexpectedly still, it turns out that, although hydroquinone is sensitive to thermal decomposition and although it is necessary to maintain the hydroquinone at temperatures of 170 to 220° C. throughout the distillation of stages (A) and (B), these stages can nevertheless be efficiently carried out while limiting the phenomena of thermal decomposition of the hydroquinone which are capable of forming colored decomposition products of quinine type.

In this context, the inventors have in particular demonstrated that stages (A) and (B) can be efficiently carried out while nevertheless limiting the residence time in the distillation columns, whereby the phenomena of thermal decomposition can be very substantially inhibited.

These decomposition phenomena can in addition be still further avoided by limiting the presence of oxygen in the distillation columns, for example while operating under an inert atmosphere.

In addition, the studies of the inventors have made it possible to establish that, under the purification conditions according to the invention, in the case where possible colored products from the thermal decomposition of hydroquinone of quinone type are formed, the latter are substantially recovered with the pyrogallol at the bottom of the column for the tailing distillation of stage (B).

According to the present invention, it has also been discovered that the pyrogallol and the impurities resulting from its decomposition can be efficiently removed during a distillation operation.

As mentioned above, the pyrogallol at least partially decomposes to give colored impurities owing to the fact that the distillation of the hydroquinone is carried out at high temperature.

It was to be feared that the colored impurities would be re-encountered, in stage (B), in the distillation top product with hydroquinone.

It has been found, according to the invention, that the pyrogallol and the impurities formed by its decomposition remain in the distillation bottom product and can thus be efficiently separated from the hydroquinone.

The invention provides a purification process which makes possible a removal of the various impurities which is both efficient and economic.

The exact composition of the crude hydroquinone $HQ^0$ treated according to stages (A) and (B) of the process of the invention can vary to a fairly large extent, the process of the invention proving, however, to be especially advantageous for crude hydroquinones comprising from 96 to 99.5% by weight of hydroquinone and contents of impurities of the order of 0.5 to 4% by weight, for example of 0.5 to 2% by weight, in particular of 1 to 2% by weight, with respect to the total weight of the crude hydroquinone.

Typically, a crude hydroquinone $HQ^0$ treated according to the invention comprises from 0.1 to 2% by weight, for example from 0.2 to 1% by weight, of light impurities (having a lower evaporation point than that of hydroquinone), including resorcinol. Resorcinol is generally a major impurity within the light impurities, the light impurities generally comprising at least 50% by weight of resorcinol, with respect to the total weight of the light impurities, for example at least 70% by weight, in particular at least 80% by weight, especially at least 90% by weight, indeed even more. In addition to resorcinol, the light impurities present in the crude hydroquinone $HQ^0$ can in particular comprise pyrocatechol.

Furthermore, in the crude hydroquinone $HQ^0$, the amount of heavy impurities (having a greater evaporation point than that of hydroquinone) is usually from 0.1 to 2% by weight, for example from 0.2 to 1% by weight. These heavy impurities include in particular pyrogallol, generally as major heavy impurity, in general in combination with other heavy impurities, in particular tars or also thermal decomposition products of hydroquinone, such as quinones. Thus, the heavy impurities generally comprise at least 50% by weight of pyrogallol, with respect to the total weight of the heavy impurities, for example at least 70% by weight, indeed even at least 80% by weight, in particular at least 90% by weight, or more.

According to a specific embodiment, the crude hydroquinone $HQ^0$ treated according to stages (A) and (B) is obtained or is capable of being obtained from a reaction mixture resulting from the hydroxylation of phenol by hydrogen peroxide in the presence of acid catalysts of the type mentioned above in the present description, after substantial removal of the pyrocatechol by distillation.

A crude hydroquinone $HQ^0$ suited to the process of the invention comprises, by weight with respect to the total amount of crude hydroquinone:

from 96 to 99.5% of hydroquinone,
from 0.1 to 2%, preferably from 0.2 to 1%, of resorcinol,
from 0.1 to 2%, preferably from 0.2 to 1%, of pyrogallol,
optionally pyrocatechol in the form of traces, typically at a content of less than 500 ppm (0.05%), preferably at a content of less than 100 ppm (0.01%).

Whatever the exact nature of the crude hydroquinone $HQ^0$ treated according to the process of the invention, the distillation stages (A) and (B) are advantageously carried out under the conditions set out below.

The topping distillation stage (A) is targeted at removing the resorcinol and preferably substantially all the light impurities present in the crude hydroquinone $HQ^0$ by entraining them at the column top, in order to recover, at the column bottom, a crude mixture M essentially comprising hydroquinone and heavy impurities which is depleted in light impurities, in particular in resorcinol.

It should be noted that the removal of the impurities at the column top is generally accompanied by the departure of a fraction of hydroquinone at the column top, which is thus not recovered in the crude mixture M which will be employed in stage (B). In order to limit this loss of hydroquinone in stage (A), it is possible in particular to vary the number of theoretical stages and the reflux ratio of the distillation column used in stage (A), whereby it is typically possible to obtain, in the process, a (lost hydroquinone/hydroquinone in the mixture M) ratio of less than 2%, for example of between 0.2 and 1%, in particular between 0.3 and 0.7%.

The feed flow rate of the crude hydroquinone $HQ^0$ in the distillation column of stage (A) can vary to a fairly large extent, in particular according to the proportions chosen for the column and the flow rate desired in fine for the purified hydroquinone. Without implied limitation, it may simply be specified that it is possible to operate with feed flow rates ranging up to 3000 kg/h, indeed up to 5000 kg/h. Typically, it is possible to employ flow rates of the order of 100 to 3000 kg/h.

In stage (A), the feed point where the crude hydroquinone $HQ^0$ is introduced is generally substantially at mid-height in the distillation column, namely with a ratio by volume of the rectification region of the column of stage (A) to the stripping region of the column of stage (A) generally of between 25:75 and 75:25, more preferably between 30:70 and 70:30, for example between 40:60 and 60:40. The term "rectification region" is understood here to mean the internal volume of the distillation column of stage (A) which is situated above the horizontal plane comprising the feed point, in contrast to the "stripping region", corresponding to the internal column volume situated below this horizontal plane.

The stream which exits at the top of the distillation column of stage (A), which essentially comprises the light impurities to be removed and a small amount of hydroquinone, can advantageously be partially diverted, in order to be reinjected into the distillation column, according to the reflux technique. The amount of stream which is reinjected into the column can be quantified by a reflux ratio, defined by the ratio of the flow rate effectively exiting at the outlet of the column top to the flow rate of material reinjected from the top of the column towards the interior of the column. In the column of the topping distillation of stage (A), this reflux ratio is advantageously between 300 and 2000, typically between 400 and 1500, for example between 500 and 1000.

Furthermore, the number of theoretical stages of the column used in stage (A) is advantageously at least equal to 20, preferably at least 30, for example between 30 and 50.

Moreover, the residence time of the hydroquinone in the column of stage (A) is preferably less than 1 hour, preferably less than 45 minutes and more preferably still less than 30 minutes, which makes it possible in particular in inhibit the phenomena of thermal decomposition of hydroquinone by limiting the time during which the latter is subjected to high temperature. Nevertheless, this residence time generally remains at least equal to 10 minutes, for example at least 15 minutes, in particular in order to make possible efficient separation of the light impurities in stage (A). A good compromise between separation and inhibition of thermal decomposition is thus obtained in stage (A) with residence times typically of the order of 15 to 30 minutes.

Stage (B), which follows stage (A), for its part consists of a tailing distillation which is targeted at removing the pyrogallol present in the crude mixture M obtained on conclusion of the topping distillation and preferably substantially all the heavy impurities. In stage (B), contrary to stage (A), it is the impurities which are sent into the column bottom and it is at the column top that hydroquinone is recovered in the purified form.

Here again, the removal of the impurities towards the column bottom is accompanied by the departure of a portion of the hydroquinone at the column bottom.

Thus, not all the hydroquinone in the mixture M is recovered at the column top. In order to limit this loss of hydroquinone at the distillation column bottom of stage (B), it is possible in particular to vary the reflux ratio and the number of theoretical stages of the distillation column of stage (B), whereby it is possible typically to obtain, in stage (B), a (lost hydroquinone/hydroquinone recovered in the purified hydroquinone) ratio of less than 2%, for example of between 0.2 and 1%.

In stage (B), the feed point where the crude mixture M resulting from the column bottom of stage (A) is introduced is in general substantially at mid-height in the distillation column. Typically, for the column of stage (B), the ratio by volume of the rectification region to the stripping region is between 25:75 and 75:25, more preferably between 30:70 and 70:30, for example between 40:60 and 60:40. Here again, the term "rectification region" is understood to mean the internal volume of the distillation column of stage (B) which is situated above the horizontal plane comprising the feed point, in contrast to the "stripping region", corresponding to the internal volume of the column situated below this horizontal plane.

Furthermore, as in stage (A), the operation is advantageously carried out at reflux in stage (B), namely by diverting a portion of the stream which exits at the top of the distillation column of stage (B), which comprises purified hydroquinone, in order to reinject the stream into the distillation column. The reflux ratio in the column of the tailing distillation of stage (B), defined by the ratio of the flow rate effectively exiting at the outlet of the column top to the flow rate of material reinjected from the top of the column into the column is advantageously between 1 and 15, typically between 3 and 12, for example between 4 and 10.

Furthermore, the number of theoretical stages of the column used in stage (B) is advantageously at least equal to 20, preferably at least equal to 30, for example between 30 and 50.

In stage (B), it is very particularly important to control the residence time of the hydroquinone in the distillation column.

Moreover, in order to prevent thermal decomposition of the product, it is generally advantageous to choose a residence time of less than 1 hour, more advantageously of less than 30 minutes, in the column of stage (B). In order to obtain efficient separation of heavy impurities in stage (B), it is, however, generally preferable to operate with residence times of the hydroquinone in the column of stage (B) of at least 10 minutes, for example between 15 and 30 minutes.

More generally, it should be rioted that stages (A) and (B) are carried out under conditions which make possible the distillation of the hydroquinone, which implies in particular that they are carried out at temperatures sufficient for the hydroquinone to exist in the liquid or gaseous state. It is indicated to avoid the presence of any cold spot below 170° C. (solidification temperature of hydroquinone) in the device in which the distillation stages (A) and (B) are carried out, which might cause phenomena of fouling of the columns harmful to the output and/or to the quality of the distillation, indeed even phenomena in which the product sets solid, which would necessitate a complete shutdown of the process and expensive operations for cleaning the plant. To this end, to be safe, it is generally preferable for all the internal regions of the distillation columns employed for stages (A) and (B) to be at least at a temperature of 175° C. and preferably at a temperature of at least 180° C., for example of at least 185° C. The majority of the regions are greater than these temperatures, in order to achieve the evaporation of the hydroquinone necessary for the distillation, the temperature nevertheless typically remaining below 220° C.

As a general rule, in order to obtain the high temperatures required, without the presence of cold spots, use is advantageously made of jacketed columns while circulating a heat-exchange fluid brought to a temperature of the order of 180 to 220° C. Mention may in particular be made, as appropriate heat-exchange fluids, of heavy esters of carboxylic acids, such as octyl phthalate, aromatic ethers, such as diphenyl ether and/or benzyl ether, biphenyl, terphenyls, other polyphenyls which are optionally partially hydrogenated, paraffinic and/or naphthenic oils, or also some oil distillation residues.

Furthermore, it is desirable to avoid as much as possible the establishment of heat bridges between the device employed according to the invention and the external environment, in order to guard against any risk of heat losses.

Furthermore, in view of the high temperatures used, it is generally desirable to avoid the presence of oxygen in the distillation stages of stages (A) and (B), in particular in order to avoid any decomposition of the hydroquinone to quinines. To this end, these stages are advantageously carried out under an inert atmosphere substantially devoid of oxygen, for example under nitrogen or else under argon, nitrogen being preferred, in particular in view of its low cost.

Moreover, in particular in order to avoid having to heat to excessively high temperatures, the distillations of each of stages (A) and (B) are advantageously carried out under reduced pressure; these pressures, which are identical or different in the distillation columns of stages (A) and (B), are typically between 50 and 100 millibar, for example between 60 and 90 millibar. The operating pressures of stages (A) and (B) can be identical or different.

The distillation of stages (A) and (B) can advantageously be carried out according to a continuous mode, in particular by injecting the crude hydroquinone $HQ^0$ to be treated at a constant flow rate at the inlet of the topping distillation column. However, it is not out of the question to carry it out according to the batchwise mode.

Whatever their exact embodiment, stages (A) and (B) result, in fine, at the top of the column of stage (B), in a purified hydroquinone HQ after condensation, obtained in the liquid state.

The purified hydroquinone obtained according to the process of the invention comprises a very low level of impurities, generally less than 4000 ppm of impurities, generally less than 3000 ppm.

According to a specific embodiment, the process of the invention can be employed in the preparation of hydroquinone of high purity, typically comprising less than 2500 ppm of impurities, preferentially less than 2000 ppm of impurities.

Such a hydroquinone of high purity advantageously comprises less than 2000 ppm of light impurities, such as resorcinol or pyrocatechol (traces), this content of light impurities preferably being less than 1500 ppm, for example between 1000 and 1500 ppm and more preferably between 300 and 1000 ppm. The content of heavy impurities is, for its part, advantageously less than 500 ppm, preferably less than 300 ppm, for example between 20 and 200 ppm.

This stage of the process of the invention makes it possible to effectively remove the impurities since the contents of resorcinol and of pyrogallol may respectively fall as far as to 300 ppm and 20 ppm and pyrocatechol can no longer be detected by the analysis.

Before the forming, it is desirable to have available a storage tank in which hydroquinone is maintained in the liquid state.

Thus, said storage tank is maintained at a temperature of between 175° C. and 190° C., preferably of between 178° C. and 185° C.

Heating is advantageously carried out by circulation of steam or of an appropriate heat-exchange fluid in the jacket. Reference may be made, as examples of heat-exchange fluids, to those mentioned above.

The storage tank is maintained under inert atmosphere, preferably under a nitrogen atmosphere.

In accordance with the process of the invention, the forming of the purified hydroquinone is carried out in a second stage of the process of the invention.

More specifically, the forming of the hydroquinone in the form of flakes is characterized in that it comprises the following stages:

depositing the hydroquinone in the liquid state as a film on a support made of a thermally conductive material or coated with a thermally conductive material, solidifying hydroquinone by bringing the support to the appropriate temperature, recovering the solidified product in the form of flakes using any appropriate means.

According to a preferred embodiment of the invention, the oxygen is removed beforehand from the chamber in which the forming operation is carried out.

Thus, the forming of the hydroquinone in the liquid state is carried out in an atmosphere freed from oxygen. According to one embodiment of the invention, an atmosphere of inert gases is established in the chamber. Recourse may be had to a noble gas, preferably argon, but it is generally preferable to use nitrogen due to its lower cost.

Once the inert atmosphere has been established, the hydroquinone in the liquid state is deposited as a film on an appropriate support.

In accordance with the process of the invention, the hydroquinone in the liquid state is deposited as a film on a support made of a thermally conductive material or coated with a thermally conductive material.

For the choice of the material, recourse is had to any material which does not react with the hydroquinone.

Furthermore, as this material has the property of conducting heat, the choice is advantageously made of a metal having a thermal conductivity of at least 10 W/m·K, preferably between 15 and 400 W/m·K. It should be noted that the upper limit does not exhibit any critical nature.

Mention may be made, as examples of materials corresponding to the abovementioned characteristics which are entirely well suited to the implementation of the process of the invention, inter alia of stainless steels.

The choice is advantageously made of stainless steels, such as austenitic steels, and more particularly stainless steels 304, 304 L, 316 or 316 L.

Use is made of a steel having at most 22% by weight of nickel, generally of between 6 and 20% by weight, preferably of between 8 and 14% by weight.

The steels 304 and 304 L have a nickel content varying between 8 and 12% by weight and the steels 316 and 316 L have a nickel content varying between 10 and 14% by weight.

Such steels are commonly used industrially.

Reference may be made, for the definition of austenitic steels, to the work by Robert H. Perry et al. [Perry's Chemical Engineers' Handbook, Sixth Edition (1984), pages 23-44].

The process of the invention is carried out by means of a device which makes possible the solidification of the hydroquinone in the liquid state on a cooled surface consisting of or coated with a conductive material which can be in the form of a conveyor belt, of one or more turntable(s) or else of a rotating cylinder.

The proportions of the apparatus come within the competence of a person skilled in the art.

The characteristics of the conveyor belt can vary widely. Thus, the length can range, for example, between 50 cm and 2 m and the width between 1 and 5 m. As regards the rate of forward progression of the belt, it can advantageously vary between 1 m/min and 20 m/min.

The thickness of the flakes is determined by controlling the feed rate of the hydroquinone and the rate of forward progression of the belt.

As regards the turntables, their diameter is usually between 150 and 400 min.

Their rotational speed is preferably chosen between 5 and 50 revolutions/min.

According to a first alternative form of the invention, the hydroquinone in the liquid state is deposited on a belt or on one of the turntables by spraying via a nozzle and more commonly by an overflow system comprising a feed trough continuously filled with hydroquinone in the liquid state so as to cause the hydroquinone to overflow, which hydroquinone falls by gravity onto the belt or turntable(s).

The hydroquinone is solidified by cooling at a temperature advantageously of between 20° C. and 80° C.

Generally, cooling is provided by spraying cold water onto the internal face of the belt which is not covered with hydroquinone.

With regard to the turntable(s), they are generally composed of a jacket in which a cooling liquid circulates, the cooling liquid preferably being water introduced at the appropriate temperature.

The hydroquinone is recovered in the form of flakes by virtue of a scraper blade.

According to another alternative form of the process which is preferred, the hydroquinone in the liquid state is deposited on a rotating cylinder.

The cylinder has dimensions which can vary widely.

Thus, the diameter can range from 0.15 to 2.5 m, preferably from 1 to 1.5 m, and the length can vary, for example, between 0.25 and 5 m, preferably 0.5 and 2 m.

The cylinder can be fed in many ways.

If the cylinder is placed, for example, in 1 to 10 cm of hydroquinone in the liquid state placed in a feed trough, the deposition on the cylinder takes place by dipping.

The cylinder rotates and carries away a thin layer of product which solidifies on the cylinder by cooling.

The cylinder rotates at a speed which is chosen according to the desired thickness of flakes and the feed temperature.

The layer will become thinner as the rotational speed increases.

The feeding of the hydroquinone in the liquid state can take place on the cylinder via an applicator roll, itself fed with hydroquinone in the liquid state.

The feeding can also be carried out on the cylinder by pouring by gravity or via a pump.

The cylinder is cooled by the circulation of water in a jacket or by spraying water inside the cylinder.

According to a characteristic of the process of the invention, the cylinder is preferably maintained at a temperature of between 20° C. and 80° C. and more preferably between 30° C. and 60° C.

The rotational speed of the cylinder advantageously varies between 0.5 and 20 revolutions/min, preferably between 3 and 6 revolutions/min.

The hydroquinone is maintained on the cylinder for a sufficient length of time for it to solidify.

Subsequently, the hydroquinone formed is recovered using any appropriate means and more particularly using a blade which scrapes the cylinder and detaches the layer of product, which is recovered by any known means, for example by gravity in a recovery tank.

Thus, a preferred embodiment of the process of the invention for the preparation of the hydroquinone flakes comprises the following stages:
  freeing from oxygen the chamber in which the forming operation is carried out,
  depositing the hydroquinone in the liquid state as a film on a cylinder maintained at a temperature of between 20° C. and 80° C.,
  maintaining the hydroquinone on the cylinder for a sufficient length of time for it to solidify,
  recovering the solidified product using any appropriate means.

According to the process of the invention, hydroquinone of high purity in the form of flakes corresponding to the characteristics given below is obtained.

More specifically, the hydroquinone is presented under the appearance of large particles which have a platelet form; these particles being referred to as "flakes".

The platelet particles correspond to a general shape factor defined in plane by a highly varied outline which can be more or less square, rectangular, round or oval.

The various flakes of varied shape are inscribed within a parallelepiped exhibiting the dimensions specified below.

The length generally varies between 0.5 and 6 cm, preferably between 1 and 3 cm.

The width, for its part, ranges between 0.5 and 3 cm, preferably between 0.5 and 1.5 cm.

The measurements are made on a sample of 20 flakes withdrawn at random.

The length and the width are determined by measurement using a graduated ruler.

The abovementioned parallelepipeds have one of their three dimensions (the thickness) much smaller than the other two (width and length).

As regards the thickness, it is between 400 µm and 1500 µm, preferably between 500 and 750 µm.

The thickness is measured using a caliper rule or a Palmer device.

It should be noted that it is not out of the question for some particles to exhibit dimensions outside the limits given above.

It should be emphasized that these large particles exhibit clean-cut edges.

One characteristic of the hydroquinone obtained is a very low level of fine particles in comparison with a presentation in the powder form.

The level of the fine particles is defined as the percentage by weight of the particles with dimensions of less than 100 µm.

Particles which pass through a sieve having a mesh size of 100 µm are regarded, according to the invention, as fine particles.

The level of the fine particles is less than 3% by weight, preferably between 0.7 and 1.5% by weight and more preferably between 0.7 and 1% by weight.

It will be specified, by way of indication, that the size of the fine particles ranges between 1 µm and 100 µm, with a median diameter situated between 20 and 30 µm.

The median diameter is defined as being such that 50% by weight of the particles have a diameter greater than or less than the median diameter.

By way of comparison, it will be mentioned that the level of the fine particles of hydroquinone in the powder form is of the order of 20% by weight, which means that the content of the fine particles (or dust) is divided by 10, indeed even 20.

In order to define the particle size of the hydroquinone obtained, the percentage by weight of the particles with dimensions of less than 2.5 mm, that is to say particles which pass through a sieve having a mesh size of 2.5 mm, is also defined.

This content is generally between 20 and 40% by weight.

By way of comparison, it will be mentioned that 100% of the hydroquinone particles in the powder form are less than 2.5 mm.

The hydroquinone flakes have a density which can be more or less high. The bulk (loose) density of the flakes is preferably at least 0.4 g/cm$^3$ and is more preferably between 0.4 and 0.6 g/cm$^3$ and generally between 0.45 and 0.55 g/cm$^3$.

The bulk (tapped) density of the flakes is preferably at least 0.5 g/cm$^3$ and is more preferably still between 0.5 and 0.8 g/cm$^3$ and generally between 0.6 and 0.7 g/cm$^3$.

The densities are measured according to the test described in the European Pharmacopeia standard [Volume 1, p. 256 (2004), 5th edition] on an undried product, with the only difference that the 250 ml test specimen is replaced with a 1 liter test specimen.

The hydroquinone obtained, although having a physical form which allows it to withstand attrition, retains a rate of dissolution compatible with subsequent use.

Thus, the rate of dissolution of the flakes varies according to the thickness of said flakes.

The dissolution time in water of an amount of flakes necessary in order to obtain a final hydroquinone concentration of the solution of 4.8% by weight varies between 10 and 30 min, according to a thickness of the flakes.

These measurements correspond to a test which consists in measuring the time necessary to dissolve said amount in water maintained at ambient temperature (20° C.) and kept stirred, for example using a propeller mixer with four inclined blades.

A similar test is carried out in order to determine the rate of dissolution of the flakes in acrylic acid.

The test consists in defining the time necessary in order to dissolve the amount of flakes which are necessary in order to obtain a final hydroquinone concentration of 2% by weight in the acrylic acid.

This rate ranges between 30 min and 1 h, according to the thickness of the flakes.

Measured under the same conditions, the rates of dissolution of the hydroquinone powder in water and in acrylic acid are respectively 9 min and 20 min.

It should be noted that the dissolution times of the hydroquinone formed according to the invention are slightly increased but this increase is acceptable by the user in view of the advantages otherwise obtained.

The invention does not rule out, subsequent to the forming stage, an additional stage which makes it possible to grade the flakes obtained.

Thus, the flakes can be introduced, for example, into a blade or bar granulator which makes it possible to reduce the size of the particles in order to have a more homogeneous distribution in the three dimensions and to thus obtain hydroquinone in the form of isotropic particles.

The term "isotropic particles" is understood to mean particles with three equivalent dimensions.

The particles obtained approach the cubic form and exhibit a side which can vary between 400 and 1500 μm, preferably between 500 and 750 μm.

Thus, the flakes can be used as intermediate to manufacture hydroquinone in the form of isotropic particles.

The hydroquinone thus obtained exhibits an increased density.

According to another more specific aspect, another subject matter of the present invention is a device for the implementation of the process of the invention which makes it possible to obtain flakes of purified hydroquinone.

This device, which is generally provided in the form of a plant of industrial dimensions, comprises:
 a first distillation column suited to the topping distillation of a crude hydroquinone HQ$^0$ according to the abovementioned stage (A), designed in order to remove the resorcinol at the column top and to recover, at the column bottom, a mixture comprising most of the hydroquinone and the heavy impurities; and
 a second distillation column suited to the tailing distillation of the abovementioned stage (B), the inlet of which is connected to the column bottom of the first column, designed in order to remove, at the column bottom, the pyrogallol present in the crude mixture originating from the column bottom of the first distillation column and in order to obtain, at the column top, the hydroquinone in purified form;
 a device which makes possible the forming in the form of flakes of the purified hydroquinone obtained at the distillation outlet, comprising a support made of a thermally conductive material or coated with a thermally conductive material which can be in the form of a rotating cylinder in combination with means for cooling the support and for recovering the hydroquinone flakes.

In this device, the two distillation columns advantageously exhibit the preferential characteristics as defined above in the present description. In particular, the columns are preferably jacketed columns heated by a heat-exchange fluid of the abovementioned type.

As regards the forming device, it is advantageously placed in a chamber equipped with means which make it possible to provide an inert atmosphere, preferably nitrogen.

The invention will be clarified still more by means of the description which follows, made with reference to the appended figures, where:

In FIG. 1, which illustrates the general principle of the process of the invention, crude hydroquinone HQ$^0$ (11), which is a mixture of hydroquinone, of light impurities comprising resorcinol and of heavy impurities comprising pyrogallol, is introduced into a first distillation column (10): the feeding of the column (10) is preferably located substantially at mid-height in the column.

The topping distillation [stage (A)] which is carried out in the column (10) results, in the column (10) top, in the removal of a stream, symbolized by (I) in FIG. 1, comprising resorcinol and optionally other light impurities, and also a fraction of the hydroquinone. This stream (I) coming from the column top can subsequently be treated, recycled or removed, in particular by a treatment in a burner. The stream (12) which exits at the column (10) top is partially diverted (13) in order to be reinjected into the column (10), generally laterally at the column top, in order to provide for reflux in the column, which reflux is installed in particular in order to improve the efficiency of the separation.

At the same time, in the column (10) bottom, a crude mixture M (14) is obtained which comprises hydroquinone and heavy impurities, with possibly traces of light impurities not extracted during the preceding stage. This crude mixture M is introduced into a second distillation column (20), the feeding of the column (20) preferably being substantially at mid-height. The crude mixture M resulting from the column (10) will be subjected, in this column (20), to the tailing distillation of stage (B).

In the column (20), the distillation results in the separation, on the one hand, of a purified hydroquinone HQ (22), recovered at the column (20) top and obtained after condensation in the liquid form, and, on the other hand, of a stream (24), symbolized by (II) in FIG. 1, comprising pyrogallol and optionally other heavy impurities (and also a small amount of hydroquinone) which are discharged at the column (20) bottom. This stream (II) which exits at the column (20) bottom is subsequently treated, removed or recycled. Here again, it is advantageous to install reflux (23) by diverting a portion of the stream (22), in particular in order to improve the efficiency of the separation of the heavy impurities.

A purified hydroquinone (22), which essentially no longer comprises impurities and which has been liquefied after passing into a condenser, is obtained at the top of the column (20).

This liquid and purified hydroquinone is subsequently stored, before being formed, in a storage tank (25) maintained under an inert atmosphere and in the liquid state.

Figure 2:
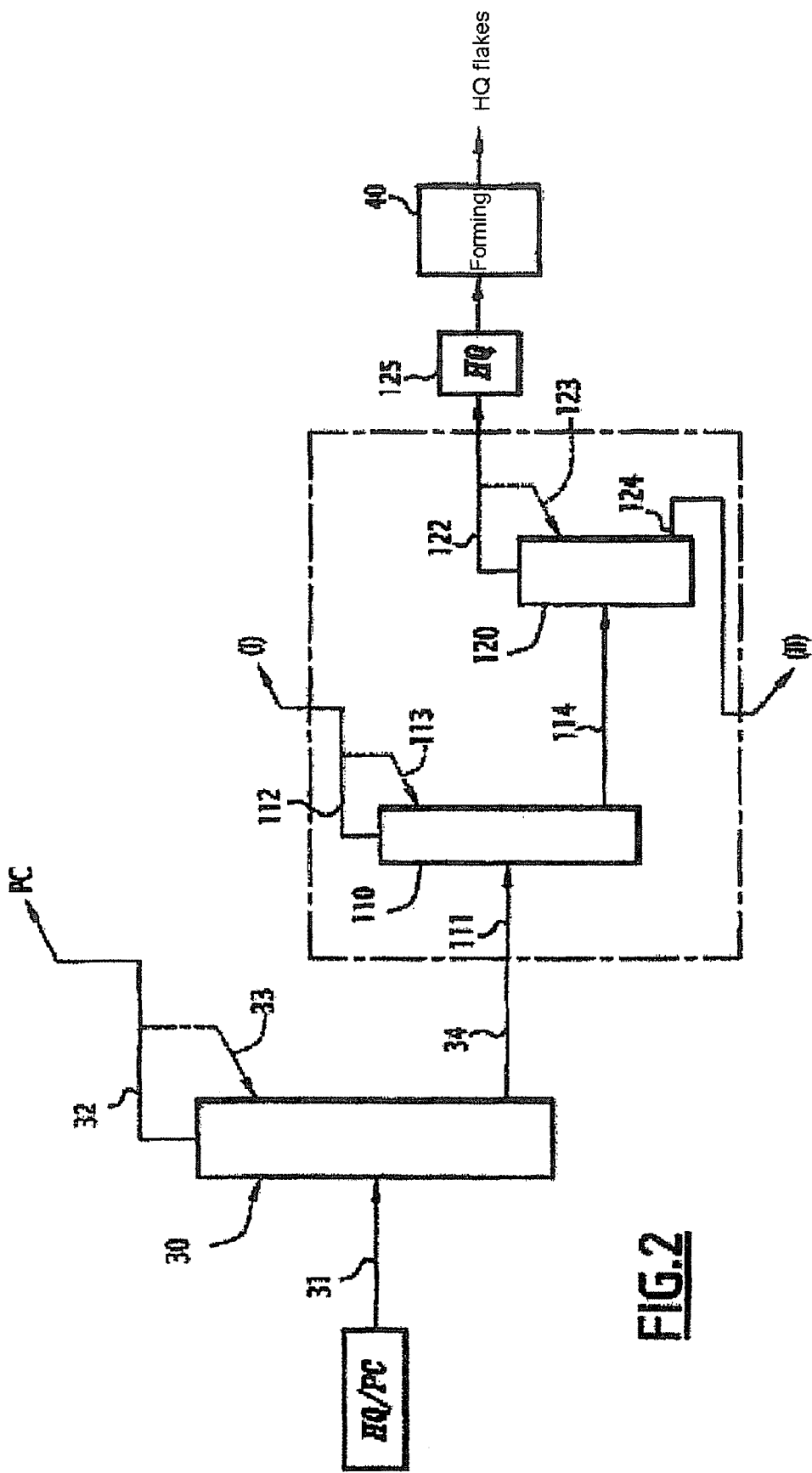
FIG. 2 is a diagrammatic representation of a device employing a specific alternative form of the invention, according to which purified hydroquinone is prepared starting from a mixture such as results from a reaction for the hydroxylation of phenol by hydrogen peroxide in the presence of a catalyst of strong protic acid type.

In FIG. 2, a device of the abovementioned type is employed in a more complex process for the treatment of an HQ/PC mixture of the type obtained on conclusion of a hydroxylation of phenol by hydrogen peroxide in the presence of a catalyst, this HQ/PC mixture essentially comprising pyrocatechol (PC) and hydroquinone and small amounts of light impurities (resorcinol) and heavy impurities (pyrogallol).

This HQ/PC mixture (31) feeds a first distillation column (30) intended to substantially remove the pyrocatechol (32) at the column top. Here again, it is advantageous to install reflux (33) by diverting a portion of the stream (32). A purified pyrocatechol (32) is obtained at the column (30) top.

Whatever the embodiment of the distillation in the column (30), a crude hydroquinone $HQ^0$ (34), essentially comprising hydroquinone (typically between 96 and 99.5%) in combination with small amounts of impurities, namely of the order of 0.1 to 2% of light impurities (resorcinol and traces of pyrocatechol) and of the order of 0.1 to 2% of heavy impurities (essentially pyrogallol), is obtained at the column (30) bottom.

This crude hydroquinone $HQ^0$ is subsequently subjected to a topping distillation treatment in the column (110), where the light impurities (resorcinol and traces of pyrocatechol) are removed at the column (110) top in the form of a stream symbolized by (I) in FIG. 2. The stream which exits at the column top (112) is partially diverted (113) in order to be reinjected into the column (110) in order to provide reflux. A crude mixture (114), comprising hydroquinone and the heavy impurities (essentially pyrogallol), is recovered at the column (110) bottom.

The crude mixture thus obtained is introduced into the column (120), preferably substantially at mid-height. It is subjected, in this column, to a tailing distillation, resulting in the recovery, at the column (120) top, of purified hydroquinone HQ (122), advantageously provided with reflux (123). For their part, the heavy impurities are removed at the column (120) bottom in the form of a stream (124) symbolized by (II) in FIG. 2.

Thus, at the outlet of the column (122), a purified hydroquinone in the liquid state is obtained and is subsequently stored in a storage tank (125) maintained under an inert atmosphere and in the liquid state.

Figure 3:
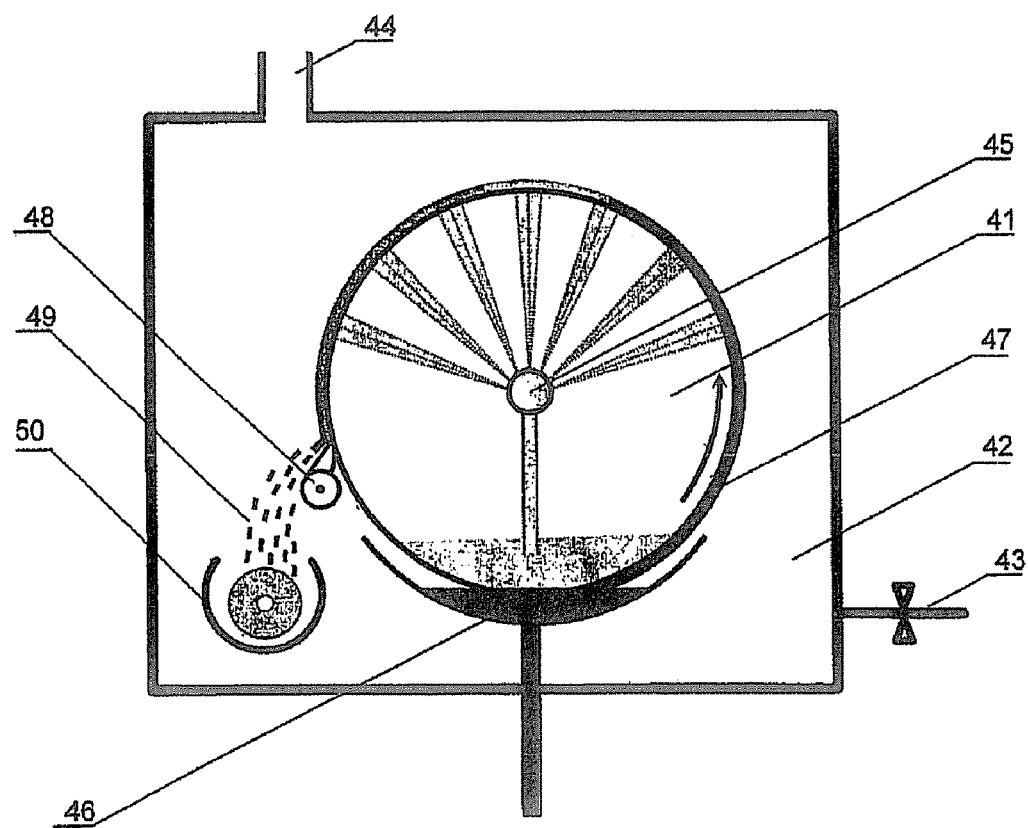
FIG. 3 is a diagrammatic representation of a device which makes possible the forming of the hydroquinone on a rotating cylinder.

It is subsequently conveyed to a forming device (40), such as represented by FIG. 3, which makes it possible finally to recover the hydroquinone in the form of flakes.

Thus, the process illustrated in FIG. 2 makes possible the efficient separation, in the isolated and purified (thus enhanced in value) form, of the two main constituents (pyrocatechol and hydroquinone) present in the reaction media resulting from a reaction for the hydroxylation of phenol by hydrogen peroxide in the presence of an acid catalyst of strong protic acid type. This process can be carried out continuously. This particular embodiment of the process constitutes a specific subject matter of the present invention.

In FIG. 3, the hydroquinone flakes are obtained by solidification of molten hydroquinone on a rotating cylinder (41) made of stainless steel (316) in a chamber (42) in which an atmosphere depleted in oxygen is established by the introduction of nitrogen (43). The gas laden with hydroquinone vapors is discharged from the chamber in the direction of a device for the treatment of the gases (44).

The temperature of the cylinder is regulated by spraying water over its internal face (45). There is no direct contact between the cooling water and the product.

The hydroquinone in the liquid state originating from the storage tank (25) or (125) is introduced into a feed tank (46), the temperature of which is regulated by a jacket in which a heat-exchange fluid circulates. The cylinder dips into the molten hydroquinone and, due to its rotation, carries away a film of molten product (47) at its external surface.

This film of product gradually solidifies on contact with the cold metal to arrive solidified at a scraping blade (48) which detaches it from the cylinder in the form of flakes (49).

The flakes thus obtained are collected in the trough of a screw conveyor (50) which removes them from the chamber.

The process of the invention makes it possible, starting from the crude hydroquinone, to obtain, in a simple and economic way, purified hydroquinone which can be easily handled.

Furthermore, the hydroquinone as obtained according to the invention exhibits a very low content of thermal decomposition products, such as quinones, in particular when the process is carried out while avoiding any contact of the heated hydroquinone with oxygen. This low content of decomposition products is reflected by a substantial absence of coloring of the purified hydroquinone obtained, which has a white appearance. The coloring of the hydroquinone can be measured more precisely by calorimetric analysis of an aqueous solution of said hydroquinone, typically by producing a 5% by weight solution at ambient temperature. It is possible to obtain low calorimetric indices of between 20 and 200 Hazen and preferably between 20 and 100 Hazen for the purified hydroquinones of the invention.

It is specified that the various percentages by weight given in the present text, with regard to the hydroquinone in a solid form, are expressed with respect to a dry product obtained after drying until a constant weight is obtained.

An embodiment of the invention, given by way of illustration without a limiting nature, is given.

EXAMPLE

1. Purification of Crude Hydroquinone:

A device as represented in FIG. 1, employed continuously, was used to purify a crude hydroquinone comprising, by weight with respect to the total weight of the crude hydroquinone, 0.6% of resorcinol and 0.7% of pyrogallol.

This mixture was introduced into the first distillation column (10) with a constant feed flow rate of 100 kg/h.

The column (10) used exhibits the following characteristics:

| | |
|---|---|
| number of theoretical stages: | 30 |
| column top temperature: | 202° C. |
| working pressure: | 87 mbar |
| reflux ratio: | 600 |

The residence time of the hydroquinone in the column (10) is evaluated at 25 min.

A stream (I) comprising resorcinol was obtained at the top of the column (10), the resorcinol having a flow rate of 1 kg/h.

The second column (20), into which the crude mixture obtained at the bottom of the first column (10) was introduced, was for its part used under the following conditions:

| | |
|---|---|
| number of theoretical stages: | 30 |
| column top temperature: | 201° C. |
| working pressure: | 73 mbar |
| reflux ratio: | 7 |

The residence time of the hydroquinone in the column (20) is evaluated at 30 min.

The stream (24) comprising the pyrogallol at the bottom of the column (20) has a flow rate of 1 kg/h.

A purified hydroquinone HQ was obtained at the top of the column (20), which hydroquinone exits with a flow rate of 98 kg/h.

This hydroquinone comprises less than 2000 ppm of resorcinol and less than 200 ppm of pyrogallol.

It thus has a purity of 99.78% by weight.

The hydroquinone obtained exhibits a coloring of 30 Hazen.

The purified hydroquinone HQ recovered at the column (22) top is stored, before being formed, in a storage tank (25) maintained under a nitrogen atmosphere and at a temperature of between 178° C. and 185° C. provided by circulation of a heat-exchange fluid in the jacket with which it is provided.

2. Forming of the Purified Hydroquinone:

The stage of forming the purified hydroquinone is carried out in the apparatus described below and represented diagrammatically by FIG. 3.

The hydroquinone flakes are obtained by solidification of molten hydroquinone on a rotating cylinder (41) made of stainless steel (316) in a chamber (42) in which an atmosphere depleted in oxygen is established by the introduction of nitrogen (43). The gas laden with hydroquinone vapors is discharged from the chamber in the direction of a device for the treatment of the gases (44).

The temperature of the cylinder is regulated by spraying water over its internal face (45). There is no direct contact between the cooling water and the product.

The hydroquinone in the liquid state originating from the storage tank (25) represented in FIG. 1 is introduced into a feed tank (46), the temperature of which is regulated by a jacket in which a heat-exchange fluid circulates. The cylinder dips into the molten hydroquinone and, due to its rotation, carries away a film of molten product (47) at its external surface.

This film of product gradually solidifies on contact with the cold metal to arrive solid at a scraping blade (48) which detaches it from the cylinder in the form of flakes (49).

The flakes thus obtained are collected in the trough of a screw conveyor (50) which removes them from the chamber.

The shaping of the hydroquinone in the liquid state is carried out on a cylinder which has a surface area of 0.75 m$^2$ (length=0.48 m; diameter=0.50 m).

The operating conditions are as follows:
the rotational speed of the cylinder: V=2 revolutions/min,
the temperature of the cooling water: Tw=60° C.,
the depth of immersion of the cylinder in the molten product: D=25 mm,
the temperature of the molten product: Tp=180° C.

Flakes are obtained with a thickness of 0.95 mm with a productive output of 98 kg/h.

The % by weight of particles passing through a sieve with a mesh size of 100 μm is 0.8%.

The loose bulk density (g/cm$^3$) is 0.52.
The tapped bulk density (g/cm$^3$) is 0.70.
The dissolution time in water at 20° C. (production of a 4.8% by weight solution) is 21 minutes.

The dissolution time in acrylic acid at 20° C. (production of a 2.0% by weight solution) is 45 minutes.

Figure 4:
FIG. 4 represents a photograph taken using a digital camera which shows the morphology of flake type of the hydroquinone obtained according to the invention.
Figure 5:
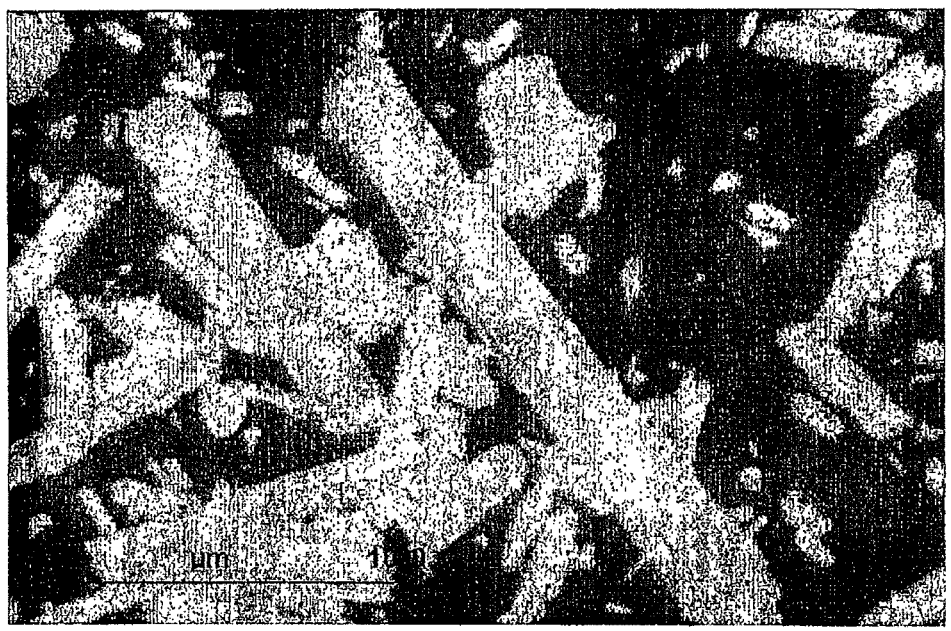
FIG. 5 represents a photograph taken using a digital camera which shows the morphology as needles of the crystals of the commercially available hydroquinone powder.
Figure 6:
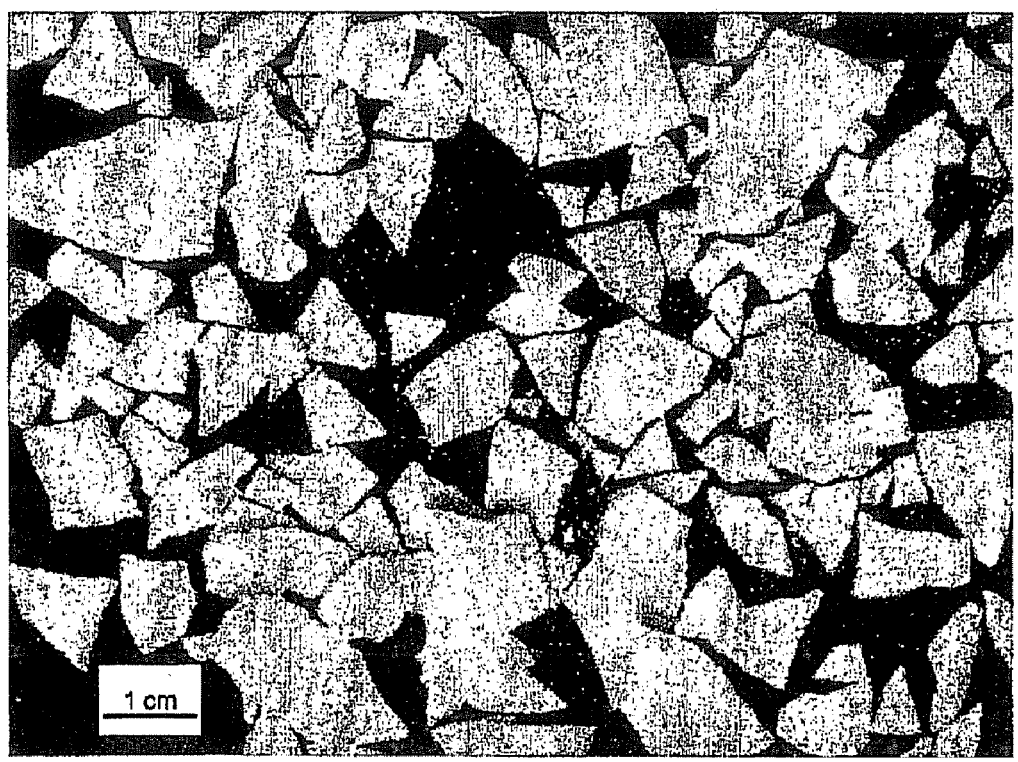
FIG. 6 represents a photograph, also taken using a digital camera, which shows a better general view of the product of the invention by virtue of a lower magnification indicated on the photograph.

The photograph of FIG. 4 illustrates the morphology of the product obtained according to the invention. A general view of the product obtained is given by FIG. 6.

What is claimed is:

1. A process for the preparation of purified hydroquinone in the form of flakes, from a crude hydroquinone essentially comprising hydroquinone and small amounts of impurities, including at least resorcinol, pyrogallol and traces of pyrocatechol, which comprises the following stages:
    a stage of purification of the crude hydroquinone by distillation, comprising:
        (A) a topping distillation, in which the crude hydroquinone HQ$^0$ is injected into a distillation column and where the resorcinol is removed as distillation top product, optionally in conjunction with all or part of the other light impurities, whereby a crude mixture M, comprising hydroquinone and the heavy impurities, is recovered at the column bottom;
        (B) a tailing distillation, in which the crude mixture M obtained in stage (A) is injected into a distillation column and where the pyrogallol is removed at the column bottom, optionally in conjunction with all or part of the other heavy impurities, whereby hydroquinone in a purified form (HQ) is recovered at the column top; and
    a stage of forming the purified hydroquinone obtained at the distillation outlet, by deposition of the latter as a film on a support made of a thermally conductive material or coated with a thermally conductive material, followed by the solidification thereof by adjusting the support to an appropriate temperature, then recovering the solidified hydroquinone in the form of flakes.

2. The process as defined by claim 1, wherein the crude hydroquinone HQ$^0$ comprises from 96 to 99.5% by weight of hydroquinone and from 0.5 to 4% by weight of impurities.

3. The process as defined by claim 1, wherein the crude hydroquinone HQ$^0$ comprises from 0.1 to 2% by weight of light impurities.

4. The process as defined by claim 1, wherein the crude hydroquinone HQ$^0$ comprises from 0.1 to 2% by weight of heavy impurities.

5. The process as defined by claim 1, wherein the light impurities present in the crude hydroquinone HQ$^0$ comprise at least 50% of resorcinol, with respect to the total weight of the light impurities.

6. The process as defined by claim 1, wherein the heavy impurities present in the crude hydroquinone HQ$^0$ comprise at least 50% of pyrogallol, with respect to the total weight of the heavy impurities.

7. The process as defined by claim 1, wherein the crude hydroquinone HQ$^0$ is obtained from a reaction mixture resulting from a hydroxylation of phenol by hydrogen peroxide in the presence of acid catalysts, after substantial removal of the pyrocatechol by distillation.

8. The process as defined by claim 1, wherein the crude hydroquinone HQ$^0$ comprises, by weight with respect to the total amount of crude hydroquinone:
    from 96 to 99.5% of hydroquinone,
    from 0.1 to 2 of resorcinol,
    from 0.1 to 2 of pyrogallol, and
    optionally, trace amounts of pyrocatechol.

9. The process as defined by claim 1, wherein stage (A), the feed point where the crude hydroquinone HQ$^0$ is introduced is substantially at mid-height in the distillation column, with a ratio by volume of the rectification region of the column of stage (A) to the stripping region of the column of stage (A) of from 25:75 and 75:25.

10. The process as defined by claim 1, wherein the stream which exits the top of the distillation column of stage (A) is partially diverted, and reinjected into the distillation column, with a reflux ratio of from 300 to 2,000.

11. The process as defined by claim 1, wherein the number of theoretical stages of the column in stage (A) is at least 20.

12. The process as defined by claim 1, wherein the residence time of the hydroquinone in the column of stage (A) ranges from 10 minutes to 1 hour.

13. The process as defined by claim 1, wherein stage (B), the feed point where the crude mixture M is introduced is substantially at mid-height in the distillation column, with a ratio by volume of the rectification region of the column of stage (B) to the stripping region of the column of stage (B) of from 25:75 and 75:25.

14. The process as defined by claim 1, wherein the stream which exits the top of the distillation column of stage (B) is partially diverted and reinjected into the distillation column, with a reflux ratio of from 1 and 15.

15. The process as defined by claim 1, wherein the number of theoretical stages of the column in stage (B) is at least 20.

16. The process as defined by claim 1, wherein the residence time of the hydroquinone in the column of stage (B) ranges from 10 minutes to 1 hour.

17. The process as defined by claim 1, wherein stages (A) and (B) are carried out under an inert atmosphere substantially devoid of oxygen.

18. The process as defined by claim 1, wherein stages (A) and (B) are carried out at pressures of from 50 and 100 millibar.

19. The process defined by claim 1, wherein an atmosphere of inert gases is established in the chamber where the hydroquinone is formed.

20. The process as defined by claim 1, wherein the material on which the hydroquinone is deposited has a thermal conductivity of at least 10 W/m·K.

21. The process as defined by claim 20, wherein the support is of or is coated with a stainless steel.

22. The process as defined by claim 20, wherein the hydroquinone in the liquid state is deposited on a cold surface coated with a conductive material is in the form of a conveyor belt, of one or more turntable(s), or of a rotating cylinder.

23. The process as defined by claim 22, wherein a cylinder is placed in 1 to 10 cm of molten hydroquinone in a feed trough and deposition on the cylinder is conducted by dipping.

24. The process as defined by claim 23, wherein the feeding of the hydroquinone in the liquid state is carried out on the cylinder via an applicator roll, itself fed with molten hydroquinone, or by pouring by gravity or via a pump.

25. The process as defined by claim 23, wherein the rotational speed of the cylinder ranges from 0.5 and 20 revolutions/min.

26. The process as defined by claim 23, wherein the cylinder is maintained at a temperature of from 20° C. and 80° C.

27. The process as defined by claim 23, wherein the cylinder is cooled by circulation of water in a jacket or by spraying water inside the cylinder.

28. The process as defined by claim 23, which comprises the following stages:
    eliminating oxygen from the chamber in which the forming operation is carried out,
    depositing the hydroquinone in the liquid state as a film on a cylinder maintained at a temperature of from 20° C. and 80° C.,
    maintaining the hydroquinone on the cylinder for a sufficient length of time for it to solidify, and
    recovering the solidified hydroquinone product.

29. The process as defined by claim 23, wherein the hydroquinone formed is recovered employing a blade which scrapes the cylinder and detaches the layer of product, which is then recovered.

30. The process as defined by claim 1, wherein the flakes obtained are subjected to a grading operation to obtain a more homogeneous distribution in the size of the particles.

31. The process as defined by claim 30, wherein the operation is carried out in a blade or bar granulator.

32. A purified hydroquinone flake, prepared by the process as defined by claim 1.

* * * * *